United States Patent [19]

Critchley et al.

[11] Patent Number: 5,198,210
[45] Date of Patent: Mar. 30, 1993

[54] COSMETIC COMPOSITION

[75] Inventors: Peter Critchley, Bedford; Desmond B. Hagan, South Wirral; Susan E. Kirsch, St. Albans; David T. Parrot, Oxton; Anthony V. Rawlings, Northants, all of England; Ian R. Scott, Allendale, N.J.; Anthony P. Taylor, Wirral, England

[73] Assignee: Elizabeth Arden Company, Division of Conopco, Inc., N.Y.

[21] Appl. No.: 781,052

[22] Filed: Oct. 21, 1991

[30] Foreign Application Priority Data

Oct. 22, 1990 [GB] United Kingdom ............... 9022922
Dec. 20, 1990 [GB] United Kingdom ............... 9027708

[51] Int. Cl.$^5$ .................. A61K 31/74; A61K 7/04; A61K 7/06
[52] U.S. Cl. .................. 424/78.03; 424/78.02; 424/70; 424/61; 514/613; 514/579
[58] Field of Search .......... 424/401, 70, 61, 78.02, 424/78.03; 514/613, 579

[56] References Cited

U.S. PATENT DOCUMENTS 4,614,748  9/1986  Taya ............................ 514/613

FOREIGN PATENT DOCUMENTS

| 0097059 | 12/1983 | European Pat. Off. . |
| 0118316 | 9/1984 | European Pat. Off. . |
| 0122152 | 10/1984 | European Pat. Off. . |
| 0227994 | 7/1987 | European Pat. Off. . |
| 0282816 | 9/1988 | European Pat. Off. . |
| 63-185441 | 1/1987 | Japan . |
| 63-185442 | 1/1987 | Japan . |
| 63-178842 | 7/1988 | Japan . |
| 63-192703 | 8/1988 | Japan . |
| 420883 | 12/1934 | United Kingdom . |

OTHER PUBLICATIONS

J. Invest. Derm., Fulmer & Kramer, (1986), 86, pp. 598–602.
Tupker, R. A. et al., Acta Derm. Venereol. Stockh, (1990), 70, pp. 1–5.
Imokana et al., J. Soc. Cosmet. Chem., 40, 273, (1980).

Primary Examiner—Thurman K. Page
Assistant Examiner—Sally Gardner
Attorney, Agent, or Firm—Milton L. Honig

[57] ABSTRACT

Novel pseudoceramides are defined, together with their synthesis and compositions comprising them for topical application to human skin, hair and nails.

6 Claims, No Drawings

COSMETIC COMPOSITION

FIELD OF THE INVENTION

The invention relates to novel pseudoceramides, their synthesis and use in compositions for topical application to human skin, hair or nails.

BACKGROUND TO THE INVENTION AND PRIOR ART

It is generally understood that ceramides present within the intercellular lipid lamellae of the stratum corneum have an important role in the production and maintenance of the water permeability barrier of the skin. Ceramides, or substances closely related to them, have been disclosed as components of skin care compositions. In particular, Kao Corporation in EP 0227994 and EP 0282816 disclose synthetic analogues of ceramides which, to a significant extent, have properties similar to natural ceramides, but are relatively cheaper to produce.

However, the degree of skin benefit attributable to such synthetic ceramides or analogues thereof is limited to the extent that they do not fully mimic the natural ceramides of the skin. Also, naturally occurring ceramides do not contain the ether bond present in most of the structures disclosed by Kao. Thus the general formula of molecules disclosed by Kao in EP 0227994 is structure (1):

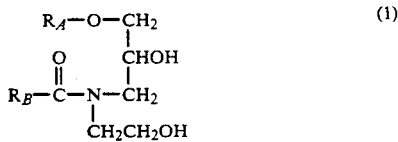

In JP-A-63-192703, Kao Corporation disclose a skin composition which contains extracted naturally occurring skin ceramides including either phytosphingosines or α-hydroxy fatty acid-containing ceramides. Synthetic hydroxylated ceramide structures are not disclosed. A further family of ceramides of the type found in skin, is disclosed in EP 097 059 (Unilever). This highlights the vital role played by ω-(0-linoleoyl) ceramides in the water barrier of the skin.

Fulmer & Kramer, in J. Invest. Derm. (1986) 86, 598-602, have observed that there is a relative deficiency of phytosphingosine-containing ceramide in detergent-induced dry skin conditions. Also, it is well documented that the stratum corneum water barrier function is impaired under such conditions (Tupker R. A. et al., Acta Derm. Venereol. Stockh [1990], 70, 1-5).

We have now discovered that the number of hydroxyl groups present within a ceramide structure is highly relevant to its influence on the water barrier properties. Furthermore, we have shown that synthetic hydroxylated ceramides, hereinafter referred to as "pseudoceramides" can be synthesised at lower cost than extracting the natural homologues from natural sources, and that these pseudoceramides posses properties necessary to improve water barrier function of the stratum corneum.

DEFINITION OF THE INVENTION

Accordingly, the invention provides a pseudo ceramide having the structure (2):

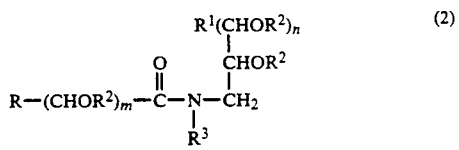

where
R represents a linear or branched, saturated or unsaturated, hydroxylated or non-hydroxylated, phosphorylated or non-phosphorylated, sulphated or non-sulphated aliphatic hydrocarbon group having from 1 to 49 carbon atoms or the sub-group $Y-O-(C_aH_b)-$;
$R^1$ represents a linear or branched, saturated or unsaturated, hydroxylated or non-hydroxylated, phosphorylated or non-phosphorylated, sulphated or non-sulphated aliphatic hydrocarbon group having from 1 to 28 carbon atoms;
$R^2$ represents H, a sugar residue, a sulphate residue or a phosphate residue $P_i$;
$P_i$ represents the group:

$R^3$ represents H, or the sub group (3):

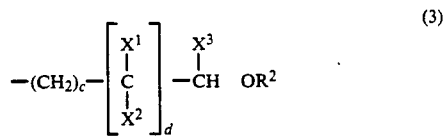

$X^1$, $X^2$ and $X^3$ each individually represent H, $C_{1-5}$ alkyl or $C_{1-5}$ hydroxyalkyl;
Y represents H or a residue of a $C_{14-22}$ fatty acid having the structure (4):

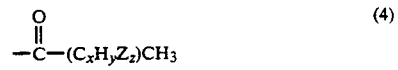

Z represents $-OH$, $-OP_i$, $-OSO_3^\ominus$ or an epoxy oxygen,
a is an integer of from 7 to 49
b is an integer of from 10 to 98
c is 0 or an integer of from 1 to 4
d is 0 or 1
x is an integer of from 12 to 20
y is an integer of from 20 to 40
z is 0 or an integer of from 1 to 4
n is 0 or 1
m is 0 or 1
provided that when the R group has from 9 to 49 carbon atoms, then n+m is 1 or 2. (If the R group has from 1 to 8 carbon atoms m and n may both be zero).

DISCLOSURE OF THE INVENTION

The Pseudoceramide

The invention provides a class of pseudoceramides having the general structure (2) as hereinbefore defined.
With reference to structure (2), the group R preferably represents an aliphatic hydrocarbon group having from 12 to 32 carbon atoms. Also, the group Y preferably represents a straight chain saturated $C_{16-18}$ fatty acid residue or a straight chain all cis n 6, 9 di-unsaturated $C_{16-18}$ fatty acid residue.

Specific examples of pseudoceramides according to the invention are those having the structures (5) to (29), as set out below:

N-(2-hydroxyoctadecyl)-N-(2-hydroxyethyl)-2-hydroxyhexadecamide having the structure (5)

$$C_{14}H_{29}-CHOH-\underset{\underset{CH_2CH_2OH}{|}}{\overset{\overset{C_{16}H_{33}}{|}}{\underset{|}{N}}-CH_2}}{\overset{O}{\underset{||}{C}}}-\overset{CHOH}{|}} \quad (5)$$

N-(2-hydroxyoctadecyl)-N-(2-0-glucopyranosyl)ethyl-2-hydroxyhexadecamide having the structure (6) (6)

N-(2-hydroxyoctadecyl)-N-(2-hydroxyethyl)-2-hydroxy-ω-0-linoleoyl docosamide having the structure (7): (7)

N-(2-hydroxyoctadecyl)-N-(2-hydroxyethyl)-2-hydroxy-ω-0-linoeoyl hexadecamide having the structure (8): (8)

N-(2-hydroxyoctadecyl)-N-(2-0-glucopyranosyl)ethyl-2-hydroxy-ω-O-linoleoyldocosamide having the structure (9): (9)

N-(2,3-dihydroxyoctadecyl)-N-(2-hydroxyethyl)-2-hydroxyhexadecamide having the structure (10): (10)

N-(2,3-dihydroxyoctadecyl)-N-(2-hydroxyethyl)hexadecamide having the structure (11): (11)

N-(2,3-dihydroxyoctadecyl)-N-(2-0-glucopyranosyl)ethyl-2-hydroxyhexadecamide having the structure (12): (12)

N-(2,3-dihydroxyoctadecyl)-N-(2-0-glucopyranosyl)ethyl hexadecamide having the structure (13): (13)

N-(2,3-dihydroxyoctadecyl)-N-(2-hydroxyethyl)-2-hydroxy-ω-0-linoleoyl docosamide having the structure (14): (14)

N-(2,3-dihydroxyoctadecyl)-N-(2-hydroxyethyl)-ω-0-linoleoyldocosamide having the structure (15): (15)

N-(2-hydroxyoctadecyl)-N-(2-sulphoethyl)-2-hydroxyhexadecamide having the structure (16): (16)

N-(2-hydroxyoctadecyl)-N-(2-phosphoethyl)-2-hydroxyhexadecamide having the structure (17):

N-(2,3-dihydroxyoctadecyl)-N-(2-phosphoethyl)-2-hydroxyhexadecamide having the structure (18)

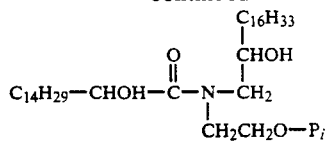
(18)

N-(2,3-dihydroxyoctadecyl)-N-(2-phosphoethyl) hexadecamide having the structure (19):

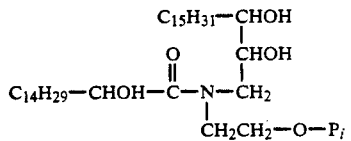
(19)

N-(2,3-dihydroxyoctadecyl)-N-(2-phosphoethyl)-2-hydroxy-ω-O-linoeoyldocasamide having the structure (20):

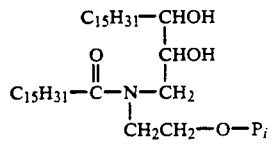
(20)

N-(2,3-dihydroxyundecyl)-N-(2-hydroxyethyl)-2-hydroxydecamide having the structure (21):

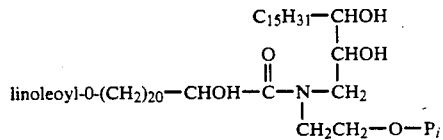
(21)

N-(2,3-dihydroxypentatriacontyl)-N-(2-hydroxyethyl)-2-hydroxypentacosamide having the structure (22):

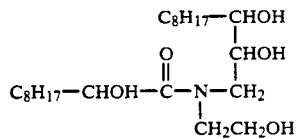
(22)

N-(2-hydroxyoctadecyl)-N-(2-0-β-D-glucopyranosido-β-D-fructofuranosyl)ethyl-2-hydroxyhexadecamide having the structure (23):

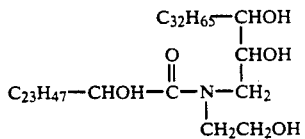
(23)

N-(2,3-diphosphooctadecyl)-N-(2-phosphoethyl)-2-phosphohexa decamide having the structure (24):

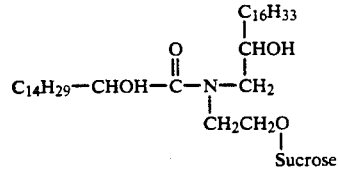
(24)

N-(2,3-disulphoctadecyl)-N-(2-sulphoethyl)-2-sulphohexadecamide having the structure (25)

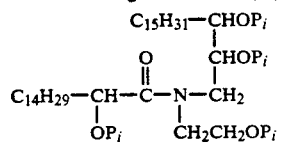
(25)

N-(2-sulpho-3,11-diphosphooctadecyl)-N-(2-phosphoethyl)-2-sulphohexadecamide having the structure (26):

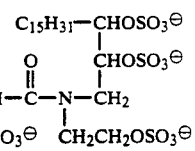
(26)

N-(2-phospho-3-sulphooctadecyl)-N-(2-phsophoethyl)-2,9-disulfohexadecamide having the structure (27):

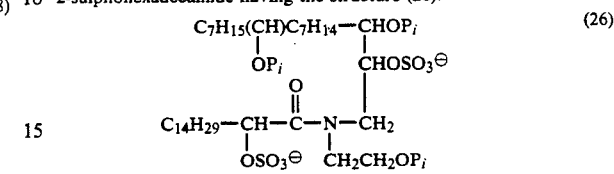
(27)

N-(2-hydroxyoctadecyl)-N-(2-hydroxyethyl)-2-hydroxy octanoamide having the structure (28):

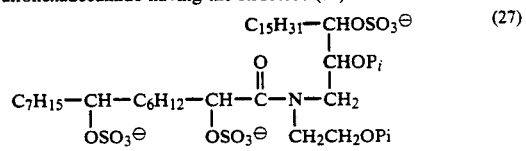
(28)

N-(2,3-dihydroxyoctadecyl)-N-(2-hydroxyethyl)-linoeamide having the structure (29):

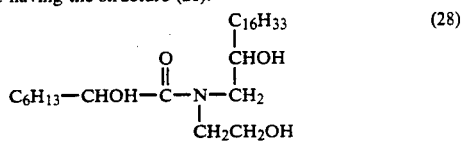
(29)

SYNTHESIS OF THE PSEUDOCERAMIDES

The pseudoceramides according to the invention can conveniently be synthesised by ring opening a terminal epoxide with an amine to provide a secondary amine. This secondary amine is then acylated with an ester or an acid chloride to obtain the required pseudoceramide.

SPECIFIC EXAMPLES OF THE SYNTHESIS

Synthesis of N-(2-hydroxyoctadecyl)-N-(2-Hydroxyethyl)-2-hydroxyhexadecamide (5)

The pseudoceramide having the structure (5), which is structure (2) with $R=C_{14}H_{29}$, $R^1=C_{16}H_{33}$, $R^2=H$, $R^3=CH_2CH_2OH$, $m=1$, and $n=0$, is prepared in accordance with this following scheme:

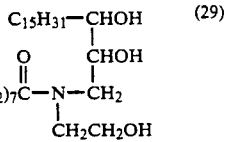

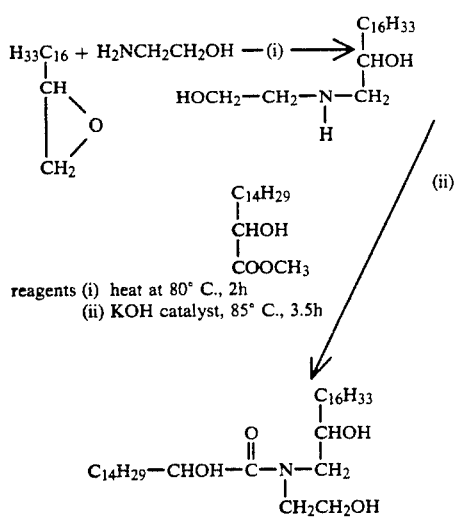

reagents (i) heat at 80° C., 2h
(ii) KOH catalyst, 85° C., 3.5h

This is essentially a two-stage process, involving the synthesis of an intermediate (30), which is then converted to the pseudoceramide (5).

Synthesis of N-(2-hydroxyethyl)-2-hydroxyoctadecylamine (30)

In a 100 ml three-necked flask equipped with dropping funnel, reflux condenser and nitrogen inlet tube, 27.0 ml (0.45 mol) of monoethanolamine were placed. While stirring and heating the mixture at 80° C. under a nitrogen atmosphere, a solution of 10.0 g (0.037 mol) of 1,2-epoxyoctadecane was added dropwise over 15 minutes. After the addition was complete, the heating and stirring was continued for an additional two hours under the same conditions. The reaction mixture was cooled to 50° C., hexane (50 ml) was added and the resulting solution was extracted at 60° C. with 2×40 ml of hot water. The hexane layer was separated; on cooling a white solid precipitated which was collected and recrystallised from first hexane and then methanol.

The intermediate (30) which was a white powdery solid, with a yield of 6.5 g (62%), possessed the following spectral characteristics:

IR (KBr) 3460, 3300, 2950, 2850, 1480, 1475 cm$^{-1}$; $^1$H NMR (CDCl$_3$) 0.88 (3H, t, CH$_3$), 1.25 (28H, bs), 1.43 (2H, m, CH$_2$), 2.15 (3H, bs, NH$_2$, OH), 2.50 (1H, dd J=13.5, 9.0 H$_z$, CH-N), 2.73 (1H, dd, J=13.5, 3.0 H$_z$, CH-N), 2.80 (2H, m, CH$_2$N), 3.65 (1H, m CH-O), 3.69 (2H, t, CH$_2$-O). (FAB) M+, 329.

Synthesis of N-(2-hydroxyoctadecyl)-N-(2-hydroxyethyl)-2-hydroxyhexadecamide (5)

In a 50 ml two-necked flask equipped with a vacuum inlet tube, 0.03g of potassium hydroxide and 2.0g (0.006 mol) of N-(2-hydroxyethyl)-2-octadecylamine (30) were placed. While stirring and heating the resultant mixture at 85° C., 20 Torr, 1.75g (0.006 mol) of methyl-2-hydroxyhexadecanoate was added portionwise over 15 minutes. After the addition was complete the mixture was stirred for a further 2.5 hours under the same conditions. The crude product was purified by two recrystallisations from hexane to give the pseudoceramide as a colourless waxy solid (2.38 g, 67%).

The purified pseudoceramide possessed the following spectral characteristics:

IR (KBr) 3380, 2950, 2850, 1630, 1470, 1080, 720 cm$^{-1}$ $^1$H NMR (CDCl$_3$) 0.88 (6H, t, 2×CH$_3$), 1.24 (52H bs), 1.44 (2H, m), 1.55 (2H, m), 3.10–4.55 (11H complex m) MS (FAB) M+, 583.

Synthesis of N-(2-hydroxyoctodecyl)-N-(2-hydroxyethyl)-2-hydroxy-ω-O-linoleoyldocosamide(7).

The pseudoceramide having the structure (7), which is structure (2) with R=Y—O—(C$_a$H$_b$)—, Y=linoleoyl, C$_a$H$_b$ is a saturated C$_{20}$ alkyl group, R$^1$=C$_{16}$H$_{33}$, R$^2$=H, R$^3$=CH$_2$CH$_2$OH, m=1 and n=0, is prepared in accordance with the following scheme:

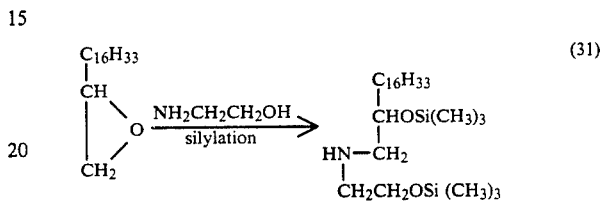

$$HO(CH_2)_{20}CHOHCOOH \xrightarrow[\text{chloride}]{\text{linoleoyl}} \quad (32)$$

linoleoyl-O—(CH$_2$)$_{20}$CHOHCOOH $$\downarrow SOCl_2$$

linoleoyl-O—(CH$_2$)$_{20}$CHOHCOC$_2$

Condensation of intermediates (31) and (32) followed by deprotection to remove the 2 trimethylsilyl ether groups yields the amide derivative having the structure (7) as follows:

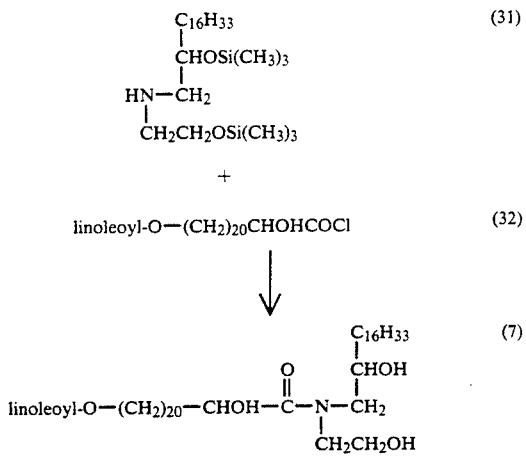

Synthesis of N-(2,3-dihydroxyoctodecyl)-N-(2-hydroxyethyl)-2-hydroxyhexadecamide (10)

The pseudoceramide having the structure (10), which is structure (2) with R=C$_{14}$H$_{29}$, R$^1$=C$_{15}$H$_{31}$, R$^2$=H, R$^3$=CH$_2$CH$_2$OH, n=1 and m=1, is prepared in accordance with the following scheme:

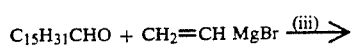

-continued

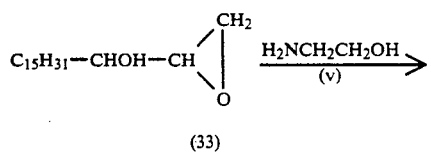

(33)

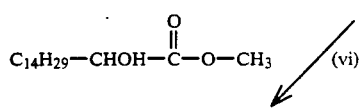

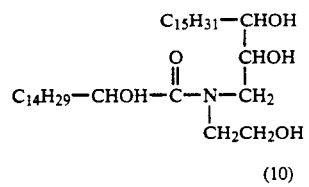

(10)

reagents
(iii) THF, −70° C.
(iv) Peracid, CH$_2$Cl$_2$
N-(2,3-dihydroxyoctodecyl)-N-(2-hydroxyethyl)-2-hydroxyhexadecamide
reagents:
(v) heat to 80° C. in ethanol.
(vi) KOH catalyst.

Synthesis of
N-(2-hydroxyoctodecyl)-N-(2-hydroxyethyl)-2-hydroxyoctanoamide (28)

This pseudoceramide has the structure (28) which is the structure (2) in which R=C$_6$H$_{13}$, R$^1$=C$_{16}$H$_{33}$, R$^2$=H, R$^3$=CH$_2$CH$_2$OH, n=0 and m=1. It is prepared as follows:

In a 50 ml two-necked flask equipped with a vacuum inlet tube, 0.01 g of potassium hydroxide and 1.0 g (0.003 moles) of N-(2-hydroxyethyl)-2-octadecylamine (29) were placed.

While stirring and heating the resultant mixture at 85° C., 20 Torr, 0.53g (0.003 moles) of methyl-2-hydroxyoctanoate was added portionwise over 30 minutes. After the addition was complete the mixture was stirred for a further 2.5 hours under the same conditions. Upon cooling, an off-white waxy solid precipitated. The solid was purified by recrystallization from hexane, followed by recrystallization from acetonitrile. The purified sample was obtained in a yield of 63%, and was a white waxy solid.

This purified solid was a mixture of four diastereomers and possessed the following characteristics:
Melting point 31.4° C.
IR 3380, 2920, 2850, 1630 cm$^{-1}$
$^{13}$C NMR (CDCl$_3$) 176.98, 68.65, 60.18, 51.43, 31.97, 29.21, 14.14

Mass spectroscopy (particle beam) confirmed the molecular weight of the product, the most abundant ion having mass 470.

DEFINITION OF COMPOSITIONS OF THE INVENTION

The invention also provides a composition for topical application to human skin which comprises:
i. an effective amount of a pseudoceramide having the structure (2); and
ii. a cosmetically acceptable vehicle for the synthetic ceramide.

DISCLOSURE OF THE COMPOSITION

The composition according to the invention comprises in its simplest form a special pseudoceramide and a vehicle therefor to enable the amide derivative to be dispersed onto the skin and distributed thereon.

The pseudoceramide

The composition according to the invention comprises an effective amount of a pseudoceramide, or a mixture thereof, having the structure (2) as herein defined.

Preferred examples of the pseudoceramide having the structure (2) are those having the structures (5) to (27), as herein defined.

The amount of the pseudoceramide, or a mixture thereof, present in the composition according to the invention is from 0.00001 to 50%, preferably from 0.001 to 20% and most preferably from 0.1 to 10% by weight.

The Cosmetically Acceptable Vehicle

The composition according to the invention also comprises a cosmetically acceptable vehicle to act as a dilutant, dispersant or carrier for the pseudoceramide in the composition, so as to facilitate its distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or oily material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | peqosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 98%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

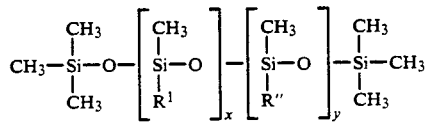

where the groups R' and R" are each chosen from —H, $C_{1-18}$ alkyl and

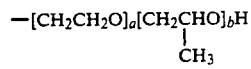

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as parahydroxy benzoate esters; antioxidants, such butyl hydroxy toluene; humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers and other ceramides of synthetic, animal or plant origin; phospholipids; waxes, such as beeswax, ozokerite wax, paraffin wax, plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the pseudoceramide, or a mixture thereof, is combined with conventional ceramides, cholesterol, cholesterol fatty acids, fatty acids, triglycerides, cerebroside, phospholipid and other ingredients well known to those skilled in the art to produce a liposomal dispersion.

In yet another preferred composition, the pseudoceramide, or a mixture thereof, is dissolved in squalene or squalane, optionally together with conventional ceramides, and formulated with volatile and non-volatile silicones to produce an anhydrous or nearly anhydrous single phase system.

Cosmetic adjuncts can form the balance of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

The modified pseudoceramides according to the invention have surfactant properties and can therefore also be used, in the form of a composition as herein defined, for cleansing the surface of the human body. In particular the composition can be used to cleanse the skin to remove make up or can be employed in a shampoo for cleansing the hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

In vitro measurement of Water Vapour Transmission Rate

The reduction in water permeability of the skin following topical application of the composition according to the invention can be determined by in vitro measurement of the water vapour transmission rate (WVTR) using a water transmission cell adapted from that described by Blank I. H., J. Invest. Dermatol., [1952], 18, 433–440.

Pretreatment of porcine stratum corneum

Isolated porcine stratum corneum was floated on propan-2-ol contained in a glass petri dish. The dish was gently agitated for 4 hours at 40° C. and the sample of extracted stratum corneum was then removed, floated in saline solution onto spectra mesh and air dried overnight.

Measurement of Initial WVTR prior to treatment

850 μl distilled water was placed in the centre well of the cell and a sample of pretreated stratum corneum (see above) was carefully laid onto a stainless steel grid over the well ensuring that the stratum corneum completely covered the O-ring, such that a watertight seal was achieved. Care was taken to avoid wrinkles, tears and holes in the stratum corneum sample. The transmission cell was then screwed into position and allowed to equilibrate at room temperature before an initial measurement was made. The cell was weighed after 5 minutes, then placed in an incubator at 37° C., 0% RH. Two further weight measurements were taken at suitable intervals over a period of 24 hours at the end of which time a test or control solution was applied and two more measurements were taken during a further 21 hours. Five cells were used for each test or control treatment.

Study of the effect of topical application of test material

For each test, a solution of test material in chloroform/methanol (2:1 v/v) was prepared at 24 mg/ml concentration 10 μl of this solution was applied to the previously selected propan-2-ol extracted skin samples as described above. The chloroform/methanol quickly e'aporated. The five cells containing the skin samples were weighed after 5 minutes prior to placing in the incubator at 37° C., 0% RH. As mentioned above, two weight measurements were then taken at intervals over a period of 21 hours.

A control measurement was made using other selected skin samples. This was carried out in the same way using an equal quantity of chloroform/methanol (2:1) containing no test material.

Calculation of the WVTR

The WVTR was calculated for each sample (pre and post topical application) as follows.

$$WVTR(mg/cm^2/hr) = \frac{\text{weight loss}}{\text{Area of exposed tissue} \times \text{time}}$$

The mean WVTR for each group of cells was then calculated from these values. The standard deviation was calculated from the observed changes (relative increase or decrease) in WVTR measured before and after the topical application.

Statistics

The level of significance was calculated using Duncan's Multiple Range test between WVTR measurements.

Results

The above procedure was used to assess the ability of solutions of pseudoceramides, namely N-(2-hydroxyoctadecyl)-N-(2-hydroxyethyl)-2-hydroxydecamide (Structure 5) and N-(2-hydroxyoctadecyl)-N-(2-hydroxyethyl)-2-hydroxyoctanoamide (Structure 28) to reduce WVTR.

These were compared with controls using chloroform/methanol alone, and positive controls using natural stratum corneum lipid in chloroform/methanol. Concentration of the natural lipid was again 24 mg/ml. Four experiments were as set out below, while in a fifth experiment the test substance was a commercial skin lotion.

| WVTR Values in mgs/cm²/hr. with Standard Deviation | | |
| --- | --- | --- |
| | before topical application | after topical application |
| Experiment 1 | | |
| a) Control (CHCl₃: MeOH only) | 11.66 ± 7.78 | 11.25 ± 5.71 |
| b) Skin lipid positive control (24 mgs/ml in CHCl₃: MeOH) | 8.97 ± 5.24 | 4.58 ± 1.97 |
| c) Pseudoceramide 28 (24 mgs/ml in CHCl₃: MeOH) | 5.62 ± 2.58 | 4.31 ± 2.03 |
| Experiment 2 | | |
| a) Control (CHCl₃: MeOH only) | 7.75 ± 4.13 | 7.58 ± 4.60 |
| b) Skin lipid positive control (24 mgs/ml in CHCl₃: MeOH) | 8.28 ± 5.17 | 4.06 ± 1.64 |
| c) Pseudoceramide 28 (24 mgs/ml in CHCl₃: MeOH) | 4.38 ± 1.77 | 2.55 ± 1.14 |
| Experiment 3 | | |
| a) Control (CHCl₃: MeOH only) | 11.35 ± 2.54 | 10.98 ± 1.74 |
| b) Skin lipid positive control (24 mgs/ml in CHCl₃: MeOH) | 12.78 ± 4.93 | 7.13 ± 2.71 |
| c) Pseudoceramide 5 (24 mgs/ml CHCl₃: MeOH) | 15.56 ± 2.31 | 8.39 ± 1.23 |
| Experiment 4 | | |
| a) Control (CHCl₃: MeOH only) | 13.33 ± 3.31 | 11.04 ± 2.87 |
| b) Skin lipid positive control (24 mgs/ml in CHCl₃: MeOH) | 15.06 ± 3.88 | 9.16 ± 2.24 |
| c) Pseudoceramide 5 (24 mgs/ml in CHCl₃: MeOH) | 10.87 ± 5.53 | 5.77 ± 3.04 |
| Experiment 5 | | |
| a) Control (CHCl₃: MeOH only) | 20.74 ± 3.40 | 15.91 ± 3.69 |
| b) Skin lipid positive control (24 mgs/ml in CHCl₃: MeOH) | 27.62 ± 15.07 | 8.53 ± 7.70 |
| c) Commercial skin lotion (24 mgs/ml in CHCl₃: MeOH) | 14.69 ± 2.52 | 13.63 ± 2.65 |

These experiments show that pseudoceramides of structures 5 or 28 significantly reduces the WVTR of the skin sample to which it was applied ($p < 0.05$) compared with commercial skin lotion.

In a similar, previous experiment a quick assessment of each cell's WVTR was made after 24 hours and used to pick out cells where the WVTR was between 4 and 5 mg/cm²/hr.

Test solutions had a concentration of 5 mg/ml and 20 pl was applied to each skin sample. Comparison was made between skin samples which received no topical application (Control 1), skin samples which received chloroform/methanol only (Control 2), skin samples which received a solution of pseudoceramide of structure 5 and skin samples which received a solution (5 mg/ml) of a triglyceride.

The WVTR values obtained in the second 24 hours, i.e. following topical application are tabulated below:

| | | WVTR (mg/cm²/hr) |
|---|---|---|
| (i) | no topical application (Control 1) | 4.6 ± 0.25 |
| (ii) | chloroform/methanol only (Control 2) | 4.6 ± 0.33 |
| (iii) | triglyceride in chloroform/methanol | 4.75 ± 0.5 |
| (iv) | Structure (5) in chloroform/methanol | 3.65 ± 0.475 |

From these results it can be deduced that the presence of Structure (5) pseudoceramide significantly reduced the WVTR of the skin sample to which it was applied (P<0.01), compared with the controls.

For purposes of comparison, it is also apparent that topical application of an triglyceride did not reduce the WVTR.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EXAMPLES

The invention is illustrated by the following examples.

EXAMPLE 1

This example illustrates a high internal phase water-in-oil emulsion in accordance with the invention.

A high internal phase water-in-oil emulsion having the following formulation was prepared:

| | % w/w |
|---|---|
| Fully hydrogenated coconut oil | 3.9 |
| Pseudoceramide having the structure (5) | 0.1 |
| Brij 92* | 5 |
| Bentone 38 | 0.5 |
| Preservative | 0.3 |
| MgSO₄7H₂O | 0.3 |
| Butylated hydroxy toluene | 0.01 |
| Perfume | qs |
| Water | to 100 |

*Brij 92 is polyoxyethylene (2) oleyl ether

EXAMPLE 2

This example also illustrates a high internal phase water-in-oil emulsion in accordance with the invention in which the formulation of Example 1 was prepared but with the following changes:
i. liquid paraffin replaced the fully hydrogenated coconut oil, and
ii. the pseudoceramide had the structure (6).

EXAMPLE 3

This example also illustrates a high internal phase water-in-oil emulsion in accordance with the invention in which the formulation of Example I was prepared but with the following changes:
The pseudoceramide had the structure (7).

EXAMPLE 4

This example illustrates an oil-in-water cream containing an ester of the invention.

An oil-in-water cream emulsion having the following formulation was prepared:

| | % w/w |
|---|---|
| Mineral oil | 4 |
| Pseudoceramide having the structure (8) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 5

This example also illustrates an oil-in-water emulsion containing a compound of the invention, in which the formulation of example 4 was prepared but with the following change: the pseudoceramide was that having structure (9), as herein defined.

EXAMPLE 6

This example also illustrates an oil-in-water emulsion in accordance with the invention, in which the formulation of example 4 was prepared but with the following changes: pseudoceramide was that having the structure (10) as herein defined.

EXAMPLE 7

This example illustrates an alcoholic lotion containing an amide of the invention.

The lotion had the following formulation:

| | % w/w |
|---|---|
| Pseudoceramide having the structure (11) | 0.2 |
| Ethanol | 40 |
| Perfume | qs |
| Butylated hydroxy toluene | 0.01 |
| Water | to 100 |

EXAMPLE 8

This example illustrates an alcoholic lotion containing an amide of the invention.

The lotion had the following formulations:

| | % w/w |
|---|---|
| Pseudoceramide having the structure (12) | 0.2 |
| Dimethylsulphoxide | 10 |
| Ethanol | 40 |
| Antioxidant | 0.1 |

-continued

|  | % w/w |
|---|---|
| Perfume | qs |
| Water | to 100 |

EXAMPLES 9 and 10

The following compositions according to the invention represent lotions which can be used in the treatment of dry skin:

|  | % w/w | |
|---|---|---|
|  | 9 | 10 |
| Pseudoceramide having the structure (13) | 1.5 | — |
| Pseudoceramide having the structure (14) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

EXAMPLES 11 and 12

The following compositions according to the invention represent lotions which can be used in the treatment of dry skin:

|  | % w/w | |
|---|---|---|
|  | 11 | 12 |
| The pseudoceramide having the structure (15) | 0.08 | — |
| The pseudoceramide having the structure (16) | — | 0.15 |
| Ethanol | 10 | 10 |
| Perfume | 0.5 | 0.5 |
| Distilled water | to 100 | to 100 |

EXAMPLE 13

This example illustrates a high internal phase water-in-oil emulsion in accordance with the invention.

A high internal phase water-in-oil emulsion having the following formulation was prepared:

|  | % w/w |
|---|---|
| Fully hydrogenated coconut oil | 3.9 |
| Pseudoceramide having the structure (17) | 0.1 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 14

This example also illustrates a high internal phase water-in-oil emulsion in accordance with the invention in which the formulation of Example 1 was prepared but with the following changes:
i. liquid paraffin replaced the fully hydrogenated coconut oil, and
ii. the pseudoceramide had the structure (18).

EXAMPLE 15

This example also illustrates a high internal phase water-in-oil emulsion in accordance with the invention in which the formulation of Example I was prepared but with the following changes:
The pseudoceramide had the structure (19).

EXAMPLE 16

This example illustrates an oil-in-water cream containing a compound of the invention.

An oil-in-water cream emulsion having the following formulation was prepared:

|  | % w/w |
|---|---|
| Mineral oil | 4 |
| Pseudoceramide having the structure (20) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 17

This example also illustrates an oil-in-water emulsion containing a compound of the invention, in which the formulation of example 4 was prepared but with the following change: the pseudoceramide was that having structure (21), as herein defined.

EXAMPLE 18

This example also illustrates an oil-in-water emulsion in accordance with the invention, in which the formulation of example 4 was prepared but with the following changes: pseudoceramide was that having the structure (22) as herein defined.

EXAMPLE 19

This example illustrates an alcoholic lotion containing an amide of the invention.

The lotion had the following formulation:

|  | % w/w |
|---|---|
| Pseudoceramide having the structure (23) | 0.2 |
| Ethanol | 40 |
| Perfume | qs |
| Butylated hydroxy toluene | 0.01 |
| Water | to 100 |

EXAMPLE 20

This example illustrates an alcoholic lotion containing an amide of the invention which is suitable for application to nails.

The lotion had the following formulations:

|  | % w/w |
|---|---|
| Pseudoceramide having the structure (24) | 0.2 |
| Dimethylsulphoxide | 10 |
| Ethanol | 40 |
| Antoxidant | 0.1 |
| Perfume | qs |
| Water | to 100 |

EXAMPLES 21 and 22

The following compositions according to the invention represent lotions which can be used in the treatment of dry, unmanageable hair.

|  | % w/w | |
|---|---|---|
|  | 21 | 22 |
| Pseudoceramide having the structure (25) | 1.5 | — |
| Pseudoceramide having the structure (26) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

EXAMPLES 23 and 24

The following compositions according to the invention represent lotions which can be used in the treatment of dry skin, hair or nails:

|  | % w/w | |
|---|---|---|
|  | 23 | 24 |
| The pseudoceramide having the structure (27) | 0.08 | — |
| The pseudoceramide having the structure (5) | — | 0.15 |
| Ethanol | 10 | 10 |
| Perfume | 0.5 | 0.5 |
| Distilled Water | to 100 | to 100 |

EXAMPLE 25

This example also illustrates an oil-in-water emulsion containing a compound of the invention, in which the formulation of example 4 was prepared but with the following change: the pseudoceramide was that having structure (28), as herein defined.

We claim:

1. A composition suitable for topical application to skin, hair or nails, which comprises:
(i) an amount of from 0.0001 to 20% by weight of a pseudoceramide having the structure (2):

$$\overset{O}{\underset{}{\overset{\|}{R-(CHOR^2)_m-C}}}-\overset{\overset{R^1(CHOR^2)_n}{|}}{\underset{\underset{R^3}{|}}{N}}-\overset{\overset{CHOR^2}{|}}{CH_2} \qquad (2)$$

where
R represents a linear or branched, saturated or unsaturated, hydroxylated or non-hydroxylated, phosphorylated or non-phosphorylated, sulphated or non-sulphated aliphatic hydrocarbon group having from 1 from 49 carbon atoms or the sub-group $Y-O-(C_aH_b)-$;
$R^1$ represents a linear or branched, saturated or unsaturated, hydroxylated or non-hydroxylated, phosphorylated or non-phosphorylated, sulphated or non-sulphated aliphatic hydrocarbon group having from 1 to 28 carbon atoms;
$R^2$ represents H, a sugar residue, a sulphate residue or a phosphate residue $P_i$;
$P_i$ represents the group:

$$-\overset{\overset{O^{\ominus}}{|}}{\underset{\underset{O^{\ominus}}{|}}{P}}=O$$

$R^3$ represents H, or the sub group (3):

$$-(CH_2)_c-\left[\overset{\overset{X^1}{|}}{\underset{\underset{X^2}{|}}{C}}\right]_d-\overset{\overset{X^3}{|}}{CH}\ OR^2$$

$X^1$, $X^2$ and $X^3$ each individually represent H, $C_{1-5}$ alkyl or $C_{1-5}$ hydroxyalkyl;
Y represents H or a residue of a $C_{14-22}$ fatty acid having the structure (4):

$$-\overset{O}{\overset{\|}{C}}-(C_xH_yZ_z)CH_3 \qquad (4)$$

z represents $-OH$ $-OP_i$, $-OSO_3^{\ominus}$ or an epoxy oxygen,
a is an integer of from 7 to 49
b is an integer of from 10 to 98
c is 0 or an integer of from 1 to 4
d is 0 or 1
x is an integer of from 12 to 20
y is an integer of from 20 to 40
z is 0 or an integer of from 1 to 4
n is 0 or 1
m is 1
provided that when the R group has from 9 to 49 carbon atoms, then n+m is 1 or 2; and
(ii) a cosmetically acceptable vehicle for the pseudoceramide.

2. A composition according to claim 1 wherein R is at least 8 carbon atoms or is the subgroup $Y-O-(-C_aH_b)-$, the group $R^1$ containing at least 8 carbon atoms and n+m is 1 or 2.

3. A method of treating skin, hair or nails which comprises applying topically thereto a composition according to claim 1.

4. A method according to claim 3 wherein the application is to skin.

5. A method of treating skin, hair or nails which comprises applying topically thereto a composition according to claim 2.

6. A method according to claim 5 wherein the application is to skin.

* * * * *